US012642964B2

(12) United States Patent
Ackermann et al.

(10) Patent No.: US 12,642,964 B2
(45) Date of Patent: Jun. 2, 2026

(54) SYSTEM COMPRISING A CONTROLLER AND AN ELECTRICAL STIMULATION SYSTEM

(71) Applicant: Matrix Muscle Support AB, Solna (SE)

(72) Inventors: Paul Wilhelm Ackermann, Enebyberg (SE); Robin Assar Juthberg, Solna (SE)

(73) Assignee: Matrix Muscle Support AB, Solna (SE)

( * ) Notice: Subject to any disclaimer, the term of this patent is extended or adjusted under 35 U.S.C. 154(b) by 339 days.

(21) Appl. No.: 18/256,394

(22) PCT Filed: Dec. 6, 2021

(86) PCT No.: PCT/SE2021/051207
§ 371 (c)(1),
(2) Date: Jun. 7, 2023

(87) PCT Pub. No.: WO2022/124963
PCT Pub. Date: Jun. 16, 2022

(65) Prior Publication Data
US 2024/0024674 A1 Jan. 25, 2024

(30) Foreign Application Priority Data
Dec. 8, 2020 (GB) ...................................... 2019319

(51) Int. Cl.
*A61N 1/04* (2006.01)
*A61N 1/36* (2006.01)
(52) U.S. Cl.
CPC ....... *A61N 1/36031* (2017.08); *A61N 1/0452* (2013.01); *A61N 1/0476* (2013.01); *A61N 1/0484* (2013.01); *A61N 1/36003* (2013.01)

(58) Field of Classification Search
CPC ........................... A61N 1/0476; A61N 1/0484
See application file for complete search history.

(56) References Cited

U.S. PATENT DOCUMENTS

2010/0004715 A1 1/2010 Fahey
2016/0325091 A1* 11/2016 Fahey .................. A61N 1/0492
(Continued)

OTHER PUBLICATIONS

Botter, Alberto et al., "Atlas of the muscle motor points for the lower limb: implications for electrical stimulation procedures and electrode positioning" Eur J Appl Physiol., 2011, pp. 2461-2471, vol. 111.
(Continued)

*Primary Examiner* — Alyssa M Alter
(74) *Attorney, Agent, or Firm* — Knobbe Martens Olson & Bear, LLP

(57) ABSTRACT

A system comprising a controller for providing and receiving signalling to and from at least one electrical stimulation, ES, system, comprising an electrode array for applying an electrical stimulation to a muscle and one or more sensors for detecting a response of the muscle; the ES system is configured to selectively operate the electrode array in one of a motor point scan mode or a stimulation mode, wherein: in the motor point scan mode a plurality of scan measurements are taken between different pairs of electrodes; and based on measurement signalling of each scan measurement, the controller is configured to identify a first stimulation electrode and a second stimulation electrode; and in the stimulation mode a plurality of stimulation signals are applied to the first and second stimulation electrodes to provide for contraction of the muscle.

20 Claims, 3 Drawing Sheets

(56)                    References Cited

U.S. PATENT DOCUMENTS

| 2018/0043159 A1 | 2/2018 | Hassan et al. |
| 2020/0155841 A1 | 5/2020 | Bhagat et al. |

OTHER PUBLICATIONS

Rushton, D N "Topical Review: Functional electrical stimulation" Physiological Measurement, Institute of Physics, Nov. 1997, vol. 18, No. 4.
Search Report for Application No. GB2019319.9 dated Sep. 8, 2021.
International Search Report for PCT/SE2021/051207 dated Mar. 22, 2022.

\* cited by examiner

Figure 1
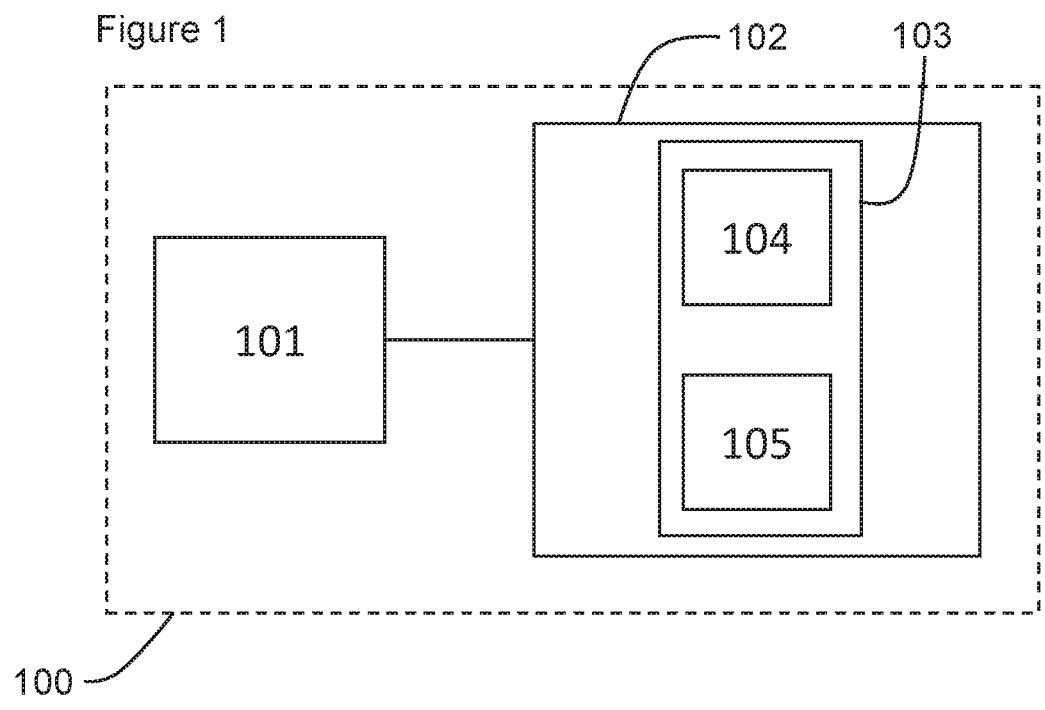
Figure 2
Figure 3
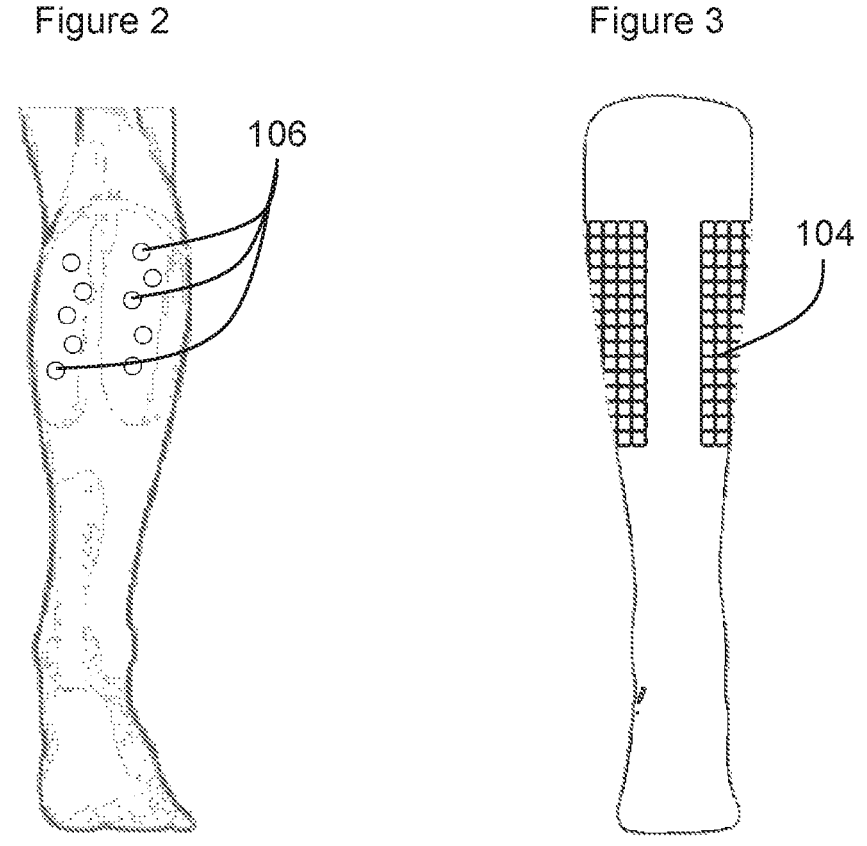

SYSTEM COMPRISING A CONTROLLER AND AN ELECTRICAL STIMULATION SYSTEM

CROSS REFERENCE TO RELATED APPLICATIONS

This application is a U.S. National Phase Application of PCT International Application Number PCT/SE2021/051207, filed on Dec. 6, 2021, designating the United States of America and published in the English language, which is an International Application of and claims the benefit of priority to United Kingdom Application No. 2019319.9, filed on Dec. 8, 2020. The disclosures of the above-referenced applications are hereby expressly incorporated by reference in their entireties.

FIELD

The present disclosure relates to a controller for an electrical stimulation (ES) system and a corresponding ES system.

BACKGROUND

Inactivity is developing into the biggest health challenge of current times. This problem is especially severe for medical patients who are immobilised. Immobilisation and muscle inactivity lead to major medical disorders, such as muscle wasting, diabetes, oedema, deep vein thrombosis and pulmonary embolism which may all lead to suffering and death. These medical disorders pose immense costs on healthcare but are potentially preventable.

Treatment of immobilisation requires mobilisation, i.e., physical activity, which may not be performed in the right amount and is not always possible for some people. In summary, low efficiency of interventions is caused by low compliance to treatment. One treatment to activate immobilised muscles is neuromuscular electrical stimulation (NMES), an example of an electrical stimulation (ES) technique, which is used by physiotherapists and, to a lesser extent, by end users to stimulate inactive skeletal muscles.

Effective application of NMES requires the correct positioning of electrodes on so-called motor points to achieve the most comfortable and least energy-consuming muscle stimulation. While motor points tend to be in similar locations across individuals, there is still a large variation in the exact position between individuals. Furthermore, even the individual motor points of a single user may vary in position from one time to another. The identification of motor points is generally performed by a NMES-trained physiotherapist by manually searching for the motor points or using their best experience and expertise to effectively guess the correct positions. Current applications of NMES lead to poor compliance in both frequency of treatment and quality of treatment.

SUMMARY

According to a first aspect of the present disclosure, there is provided a controller for providing signalling to and receiving signalling from at least one electrical stimulation, ES, system, comprising an electrode array of a plurality of electrodes for applying an electrical stimulation to a muscle and one or more sensors for detecting a response of the muscle to said electrical stimulation;

wherein the controller is configured to provide signalling to the ES system to selectively operate the electrode array in one of a motor point scan mode or a stimulation mode, wherein:

the motor point scan mode comprises a mode wherein the signalling causes a plurality of scan measurements to be taken between different pairs of the plurality of electrodes wherein each scan measurement comprises:

providing a first measurement voltage to one electrode of the pair and providing a second measurement voltage to the other electrode of the pair, the first measurement voltage different to the second measurement voltage to provide the electrical stimulation to the muscle between the electrode pair; and based on a measurement performed by the one or more sensors, providing measurement signalling to the controller indicative of the response to the electrical stimulation for said pair of electrodes, based on the measurement signalling of each scan measurement received by the controller, the controller is configured to identify a first stimulation electrode and a second stimulation electrode wherein each of the first stimulation electrode and second stimulation electrode is aligned with a different motor point of the muscle of the user; and the stimulation mode comprises a mode wherein the signalling causes a plurality of stimulation signals to be applied, wherein each stimulation signal comprises:

an application of a first stimulation voltage to the first stimulation electrode and a second stimulation voltage to the second stimulation electrode to provide the electrical stimulation to the muscle between the first and second stimulation electrodes and wherein the first simulation voltage is different to the second stimulation voltage.

In one or more embodiments, the ES system may further comprise a first garment wherein the garment provides a support for the relative arrangement of the electrodes and sensor or sensors and the garment is configured to distribute at least the electrodes over at least a body part of the user.

In one or more embodiments, during the stimulation mode, the controller may be configured to provide signalling to the ES system such that, for each stimulation signal after a first stimulation signal, the polarity of the first stimulation voltage and the second stimulation voltage is swapped as compared to the preceding stimulation signal.

In one or more embodiments, during the stimulation mode, the controller may be configured to provide signalling to the ES system such that the first stimulation voltage and the second stimulation voltage are each applied as square waves.

In one or more embodiments, the contemporaneous application of identical voltages to a plurality of electrodes in the electrode array may define a group-electrode and wherein the controller may be configured to provide signalling to the ES system to operate the electrode array in a group-electrode motor point scan mode, wherein:

the group-electrode motor point scan mode comprises a mode wherein the signalling causes a plurality of scan measurements to be taken between different pairs of group-electrodes of the electrode array wherein each scan measurement comprises:

providing a first measurement voltage to one group-electrode of the pair and providing a second measurement voltage to the other group-electrode of the pair, the first measurement voltage different to the second measurement voltage to provide the electrical stimulation to the muscle between the electrode pair, and based on a measurement performed by the one or more sensors, providing measurement signalling to the controller indicative of the response to the electrical stimulation.

In one or more embodiments, based on the measurement signalling of each scan measurement received by the controller from the ES system during a group-electrode motor point scan mode, the controller may be configured to identify a plurality of secondary group-electrodes, wherein each secondary group-electrode is comprised of fewer electrodes than each group-electrode of the previous group-electrode motor point scan and each of the secondary group-electrodes is aligned with a motor point of the muscle of the user, and wherein the controller is configured to provide signalling to the ES system to operate the electrode array in a group-electrode motor point scan mode using the determined plurality of secondary group-electrodes.

In one or more embodiments, based on the plurality of sets of measurement signalling received by the controller from the ES system during a group-electrode motor point scan mode, the controller may be configured to identify a sub-set of electrodes wherein each electrode of the sub-set of electrodes is associated with a motor point of the muscle of the user, and wherein the controller is further configured to provide signalling to the ES system to operate the electrode array in a motor point scan mode using only the sub-set of electrodes.

In one or more embodiments, based on measurement signalling of each group-electrode scan measurement, the controller may be configured to identify a first stimulation group-electrode and a second stimulation group-electrode wherein each of the first stimulation group-electrode and second stimulation group-electrode is aligned with a different motor point of the muscle of the user and, and wherein the controller may be configured to provide signalling to cause the ES system to operate the electrode array in a group-electrode stimulation mode, wherein the group-electrode stimulation mode comprises a mode wherein the signalling causes a plurality of stimulation signals to be applied to the identified group-electrodes, wherein each stimulation signal comprises:

an application of a first stimulation voltage to the first stimulation group-electrode and a second stimulation voltage to the second stimulation group-electrode to provide electrical stimulation to the muscle between the electrode pair and wherein the first stimulation voltage is different to the second stimulation voltage.

In one or more embodiments, at least one of the one or more sensors may comprise one of:

a flex sensor, wherein the flex sensor is arranged such that it will flex upon contraction of the muscle and wherein the controller is configured to receive measurement signalling indicative of the degree of flex of the flex sensor and wherein the controller is configured to identify the first and second stimulation electrodes based on the pair of first and second electrodes which provided for a flex above a flex reaction threshold as measured by the flex sensor.

a fiber optic light sensor comprising an optical fiber, wherein the fiber optic light sensor is arranged such that the optical fiber of the fiber optic light sensor will alter light transmission properties of the fiber optic light sensor upon contraction of the muscle and wherein the controller is configured to receive measurement signalling indicative of a degree of contraction of the fiber optic light sensor and wherein the controller is configured to identify the first and second stimulation electrodes based on the pair of first and second electrodes which provided change in the optical transmission of light via the optical fiber above or below a predetermined optical transmission threshold as measured by the fiber optic light sensor.

a microphone sensor, wherein the microphone sensor is arranged such that it will detect one or more of sound and vibration upon contraction of the muscle and wherein the controller is configured to receive measurement signalling indicative of a motion in the muscle from the microphone sensor and wherein the controller is configured to identify the first and second stimulation electrodes based on the pair of first and second electrodes which provided for one or more of a sound and a vibration level above one or more of a respective sound threshold and a vibration threshold as measured by the microphone sensor.

a microphone sensor, wherein the microphone sensor is arranged such that it will detect one or more of changes in sound and/or vibration originating from changes in blood flow in blood vessels associated with the muscle upon one or more of stimulation and contraction of the muscle and wherein the controller is configured to receive measurement signalling indicative of changes in blood flow from the at least one microphone sensor and wherein the controller is configured to identify the first and second stimulation electrodes based on the pair of first and second electrodes which provided for a blood flow above a blood flow threshold as measured by the microphone sensor.

In one or more embodiments, at least one of the one or more sensors may be an electrical parameter sensor, wherein the electrical parameter sensor is one of:

a resistivity sensor arranged and configured to determine an electrical resistivity and wherein the controller is configured to identify the first and second stimulation electrodes based on the pair of electrodes which provide for a resistivity below an acceptable resistivity threshold;

a resistance sensor arranged and configured to determine an electrical resistance and wherein the controller is configured to identify the first and second stimulation electrodes based on the pair of electrodes which provide for a resistance below an acceptable resistance threshold;

a conductivity sensor arranged and configured to determine an electrical conductivity and wherein the controller is configured to identify the first and second stimulation electrodes based on the pair of electrodes which provide for a conductivity above an acceptable conductivity threshold;

a conductance sensor arranged and configured to determine an electrical conductance and wherein the controller is configured to identify the first and second stimulation electrodes based on the pair of electrodes which provide for a conductance above an acceptable conductance threshold; and an impedance sensor arranged and configured to determine an electrical impedance and wherein the controller is configured to identify the first and second stimulation electrodes based on the pair of electrodes which provide for an impedance below an acceptable impedance threshold.

In one or more embodiments, one of the electrodes of the electrode array may be configured to operate as an electrical parameter sensor.

In one or more embodiments, a plurality of the electrodes of the electrode array may be configured to operate as electrical parameter sensors.

In one or more embodiments, the controller may be configured to: provide signalling to cause the ES system to operate in a baseline stimulation mode wherein, in the baseline stimulation mode, the controller is configured to receive measurement signalling from the ES system when no voltages are applied to the electrodes in response to signalling from the controller and the controller is configured to record the received measurement signalling as calibration signalling wherein, during operation in the stimulation mode, the controller is configured to compare the measurement signalling to the recorded calibration signalling and:

if the measurement signalling is not within a predetermined threshold of the calibration signalling, the controller is configured to increase the magnitude of the voltage applied to the first and second electrodes during the application of a subsequent stimulation signal.

if the measurement signalling is within a predetermined threshold of the calibration signalling, the controller is configured to apply the same voltage to the first and second electrodes during the application of subsequent stimulation signals as the voltage which caused the measuring signalling to be within the predetermined threshold of the calibration signalling.

In one or more embodiments, the electrode array may be a first electrode array and ES system further comprises a second electrode array of a plurality of electrodes for applying electrical stimulation to the muscle and one or more second sensors for detecting a response of a muscle to said electrical stimulation, wherein the first electrode array and second electrode array are arranged in the ES system to stimulate different muscles, wherein the controller is configured to provide signalling to cause the ES system to selectively operate the second electrode array in one of the motor point scan mode or the stimulation mode.

In one or more embodiments, the controller may be configured to cause the ES system to operate in a sequential stimulation mode, wherein the sequential stimulation mode comprises a mode wherein the signalling causes a plurality of stimulation signal sequences to be applied to the first electrode array and the second electrode array, wherein each stimulation signal sequence comprises:

an application of the first stimulation voltage to the first stimulation electrode of the first electrode array and a second stimulation voltage to the second stimulation electrode of the first electrode array to provide the electrical stimulation to the muscle between the first stimulation electrode and the second stimulation electrode; and wherein the first simulation voltage is different to the second stimulation voltage followed by an application of a first stimulation voltage to the first stimulation electrode of the second electrode array and a second stimulation voltage to the second stimulation electrode of the second electrode array to provide electrical stimulation to the muscle between the first stimulation electrode and the second stimulation electrode of the second electrode array, wherein the first simulation voltage is different to the second stimulation voltage and wherein the first voltage and the second voltage applied to the first and second electrodes of the second electrode array are one of:

the same magnitudes as the first voltage and second voltage applied to the first electrode and second electrode of the first electrode array and different magnitudes to the first voltage and second voltage applied to the first electrode and second electrode of the first electrode array.

In one or more embodiments, the controller may be configured to cause the ES system to operate in a monitoring mode wherein, during the monitoring mode, the controller is configured to provide signalling to cause the ES system to apply voltages at any of the electrodes and the controller is further configured to receive signalling from the one or more sensors one of continuously; and periodically and wherein, if the controller receives no indication of user-induced stimulation within a predetermine monitoring time, the controller is configured to cause the ES system to operate in the stimulation mode.

According to a second aspect of the present disclosure, there is provided an electrical stimulation, ES, system for receiving signalling from and providing signalling to a controller of the first aspect, the ES system comprising an electrode array of a plurality of electrodes configured to apply electrical stimulation to the muscle and one or more sensors for detecting a response of a muscle to said electrical stimulation.

In one or more embodiments, the ES system may further comprising a garment wherein the garment provides a support for the relative arrangement of the electrodes and sensor or sensors and is configured to distribute at least the electrodes over at least a body part of the user.

According to a third aspect of the present disclosure, there is provided a system comprising the controller of the first aspect and the electrical stimulation system of the second aspect.

According to a fourth aspect of the present disclosure, there is provided a computer readable medium comprising computer program code configured to cause a controller to operate according to the controller of the first aspect.

BRIEF DESCRIPTION OF THE DRAWINGS

One or more embodiments will now be described by way of example only with reference to the accompanying drawings in which:

FIG. 1 shows an example embodiment of a system of the present disclosure comprising a controller and an ES system;

FIG. 2 shows an example representation of motor points on the calf of a user;

FIG. 3 shows an example embodiment of an electrode array on the calf of a user;

DETAILED DESCRIPTION

Figure 4:
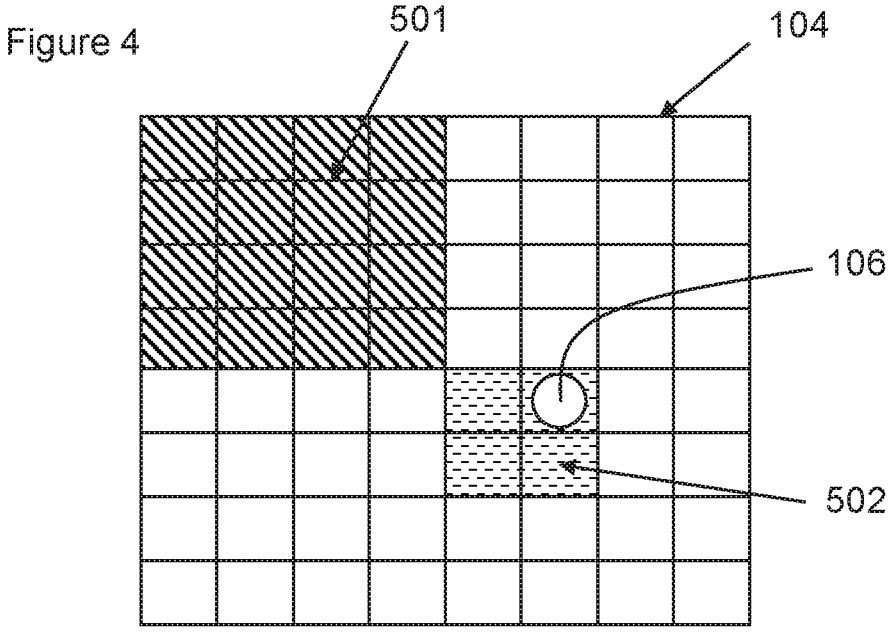
FIG. 4 shows an example embodiment of group-electrodes defined in an electrode array

As shown in FIG. 1, in the present disclosure there is described a system 100 comprising a controller 101 and an electrical stimulation, ES, system 102. The ES system 102 comprises an electrode array 104 and one or more sensors 105. In one or more embodiments, the ES system 102 may further comprise a garment 103. In one or more embodiments, the ES system 102 may comprise a plurality of garments 103, wherein each garment comprises a corresponding electrode array 104 and one or more sensors 105 or a single garment may comprise a plurality of electrode arrays 104 and associated one or more sensors 105.

The controller 101 may be any appropriate electronic controller 101 that is configured to provide signalling to and receive signalling from the ES system 102 or any component of the ES system 102. The controller 101 may comprise at least one processor and at least one memory including computer program code. The at least one memory and the computer program code may be configured to, with the at least one processor, cause the controller 101 to provide for signalling to the ES system 102. The controller 101 may also be configured to receive signalling from the ES system 102 and process the received signalling such that the controller 101 can act on the information comprised within the signalling. The actions that the controller 101 can take based on the received signalling will be described in greater detail below. It will be appreciated that any suitable means may be used by the controller 101 to provide for provision and receipt of signalling. For example, the controller 101 may be electrically coupled to the ES system 102 such that signals are transmitted directly via physical conducting means such as wires, conductive tracks, conductive fibres or conductive fabrics. Alternatively, the controller 101 may provide for signalling to cause a wireless transceiver to provide for the transmission and receipt of signalling to the ES system 102 and the ES system 102 may comprise a corresponding transceiver configured to both transmit and receive signalling. In such examples, the ES system 102 may comprise an ES controller (not shown) configured to interpret the signalling received from the controller 101.

In some examples, the controller 101 may be incorporated into one of the one or more garments 103 or may be a remote device such as a hip-mounted control box or a computing device such as a mobile phone, tablet computer, laptop computer or personal computer (PC) that may provide for communication with the one or more garments 103 of the ES system 102.

Electrical stimulation (ES) covers a range of techniques which involve providing stimulation to one or more muscles by the application of one or more electrical signals or pulses. In this description, neuromuscular electrical stimulation (NMES) will be referred to in general, however, it will be appreciated that any suitable electrical stimulation technique may be used. Other examples of suitable electrical stimulation techniques may include, but are not limited to, electrical muscle stimulation (EMS), Russian electrical stimulation, functional electrical stimulation (FES) and transcutaneous electrical nerve stimulation (TENS).

In one or more examples, the plurality of electrodes of the electrode array 104 may be configured to be connected directly to the user by any suitable means. For example, a plurality of individual electrode pads may be attached to the user and those electrodes together define the array of electrodes 104. In such embodiments, the controller 101 may be connected to the electrodes of the electrode array 104 in any suitable manner. The one or more sensors 105 may be coupled to the electrodes of the electrode array 104 or they may be separately affixed to the user. In other examples, a garment 103 may provide support for the relative arrangement of electrodes of the electrode array 104. The garment 103 may also provide for support and arrangement of the one or more sensors 105. The garment 103 may, for example, be an article of clothing, a wrapping or adhesively attached pad configured to be worn by the user.

It will be appreciated that, herein, the user is defined as the person or animal to which electrical stimulation is to be applied. This does not exclude one or more other people assisting the user, such as medical practitioners. It may even be that the user is not conscious and not operating the system 100 at all but that others, such as medical practitioners, are providing any necessary input to the system.

In examples where the NMES system 102 comprises a single garment 103, the system 100 as a whole may be entirely incorporated into a garment 103 itself such that the controller 101 comprises a microprocessor embedded into garment 103 along with the electrode array 104 and the one or more sensors 105 of the NMES system 102. In other examples, the overall system 100 may comprise a plurality of garments 103 wherein each of the electrode array 104 and the one or more sensors 105 of each garment is in signalling-communication with the controller 101. In embodiments where the NMES system 102 comprises a plurality of garments 103, the controller 101 may be incorporated into one of the garments 103 or may be incorporated into a device remote from any of the garments 103 of the NMES system 102.

The technique of neuromuscular electrical stimulation can be used to prevent several undesirable medical afflictions as discussed already or to improve bodily functions. Correctly applied NMES helps to reduce the impact and likelihood of these afflictions taking effect by both: stimulating the muscles and thereby causing them to work and either get stronger or maintain their current strength; and by forcing the movement of blood through the veins which also improves arterial circulation. The additional assistance of moving the blood may be particularly beneficial and helpful for some users for whom blood circulation is below desirable levels.

A garment 103 herein refers to an article which can be worn on a human or animal body where the human or animal wearing the garment 103 is defined as the user of the NMES system 102. It will be appreciated that garments 103 may include articles of clothing such as socks, gloves, tights, boxer shorts, long johns, vests or other articles of clothing. Alternatively, the garment 103 may be a bandage, a cast or another medical wrapping or support garment which may be applied to a human or animal body for prolonged periods and during normal activities of the user. The garments 103 referred to herein are configured to provide for support for the relative arrangement of electrodes of an electrode array 104 and one or more sensors 105 in order to distribute at least the electrodes over at least part of a body of a user. The garment 103 may be configured to distribute the electrodes of the electrode array 104 such that each electrode is in contact with the skin of a user such that the application of two different voltages at two different electrodes of the electrode array 104 causes stimulation of a muscle or its innervation below the skin, if present. In the case where a muscle or its innervation is located beneath the skin with which the electrodes are in electrical communication, the muscle may be caused to contract in response to the electrical stimulation. The stimulation of a muscle can be performed by its innervation, which refers to the electrical stimulation of an adjacent or distant nerve connected to the muscle.

FIG. 2 shows an example of the leg of a human user. Each muscle in the body comprises one or more motor points 106. The motor points 106 are defined as the areas of the skin above the muscle or its innervation which require the lowest electrical stimulation to cause a muscle twitch or contraction. Herein a motor point 106 of a muscle may refer to a point that connects to a nerve that, when electrical stimulation is applied thereto, provides for contraction of the muscle by innervation. For example, the calf muscle may comprise a plurality of different motor points 106. Power can be saved in an NMES device by accurately targeting motor points 106 of a user for electrical stimulation, thereby increasing the lifetime of an NMES system 102 of the present disclosure before recharging is required. Further, it has been found that discomfort of a user is reduced when the motor points 106 are electrically stimulated as compared to stimulating non-motor points. Electrical stimulation at a pair of motor points, as defined herein, may also provide for increased blood flow in a user while providing for stimulation of a muscle. In some examples, the optimum points for stimulation may not be optimum points for achieving the greatest possible muscle contraction or for the lowest possible current requirement for stimulation. Nevertheless, since such selected points provide for an optimum desired result, such points will also be referred to herein as motor points. It may be particularly advantageous to provide for stimulation at the motor point 106 associated with both of the electrodes used in the application of NMES as opposed to only placing a single electrode at a motor point 106 while a second electrode is placed at a non-motor point position. The present system 100 may provide for the identification of the optimal pairs of points for the provision of electrical stimulation to cause the muscle to contract. This may provide for the points on the body which are most comfortable for the user to have stimulated and which use the least energy to cause a desirable degree of contraction of the muscle. In some cases, one or both of these points may not be identified as a motor point 106 using traditional methods because traditional methods operate by manually searching for a single point relative to a fixed reference point such as by using motor point pens. In contrast, the system 100 described herein defines motor points by using a motor point scan mode to search for one or more optimum pairs of points. That is, the motor points as defined herein will be those points which provide for an advantageous result in terms of one or more desired stimulation parameters. The one or more desired stimulation parameters may include, but are not limited to: maximum muscle contraction; lowest current required for a desired level of contraction; and maximum induced blood flow. As such, one may consider the motor points herein as optimum stimulation points for achieving a desired effect.

In one or more examples, it may be the case that a location over a muscle that is identified as a motor point using a traditional motor point identification technique, such as by using a motor point pen, may not be identified as a motor point using the approach disclosed herein. Traditional approaches that, in some cases, reuse a same standard reference electrode for each measurement in order to find a single motor point may not provide the same flexibility in identifying optimal pairs of locations. In fact, in some examples, motor points identified by the herein disclosed approach may select two entirely different locations for motor points compared to traditional approaches.

FIG. 3 shows an example leg of a user and the arrangement of an electrode array 104 thereon. The garment 103 and any additional sensors 105 are not shown for clarity. The electrode array 104 comprises a plurality of electrodes which are configured to be, when in use, in electrical contact with the skin of a user. It will be appreciated that this may generally mean that the electrodes are in direct physical contact with the skin of the user but that in other embodiments, one or more conductive materials may be disposed between each electrode and the skin in use.

The electrode array 104 may be arranged in any manner which is suitable for providing stimulation to a plurality of different points on the muscle. In one or more embodiments, the electrodes may be arranged in a matrix arrangement, as shown in FIG. 3. In the matrix arrangement, the electrodes may be arranged in a regular grid pattern in order to provide for comprehensive coverage of the muscle being targeted. Each electrode in the array of electrodes 104 may be individually addressable so that a voltage can be applied at each electrode in isolation from each other electrode. Each electrode in the electrode array 104 may be electrically isolated from each of the other electrodes when the electrodes are not placed in electrical contact with a conductive medium such as skin and, when in contact via the skin, a high resistivity contact is made therebetween. When an electrode does not have a voltage applied thereto as a result of signalling from the controller 101, the electrode may be uncoupled from any voltage source or ground of the NMES system 102 such as by the opening of a switch. This may remove any chance that a current would flow between the wrong electrodes. The isolation of each of the unconnected electrodes may be controlled by the controller 101. The array of electrodes 104 may comprise, for example, more than 10, 20, 50 or 100, 225 or any other number of electrodes.

The controller 101 may provide signalling to the NMES system 102 to selectively operate the electrode array 104 in one of a plurality of modes, such as in a motor point scan mode or a stimulation mode. In either of these two modes, different voltages are applied to two different electrodes in the electrode array 104. The application of an electrical potential difference between these two electrodes provides for the stimulation of the muscle. The voltages may be applied at opposing polarities which is to say that one voltage is a positive voltage while the second is a negative voltage relative to a reference voltage such as a ground voltage. The reference voltage may be considered to be a voltage part way between the two different voltages applied to the first and second electrodes and, as such, the voltages may be at opposing polarities. It will be appreciated that, relative to another reference voltage, the voltages may be measured as having other values, such as 0 V and +5 V. It will be appreciated that, no matter the reference voltage selected, it is the presence of an electrical potential difference between the electrodes which provides for the electrical stimulation. It may be considered that electrodes that do not have a voltage applied to them as a result of signalling provided by the controller 101 are substantially at a reference voltage, such as ground or those electrodes may be disconnected from the circuit entirely. In some examples, in order to create the electrical potential difference between the selected electrodes, the voltages applied to the electrodes may be applied contemporaneously.

The one or more sensors 105 of the NMES system 102 are configured to detect a response of a muscle to electrical stimulation. Several different types of sensors may be used to measure the response of a muscle to electrical stimulation. Each of the below-described types of sensors 105 may be used individually in determining the response of the muscle or a plurality of a single type of sensor 105 may be used positioned at different points within the garment. In other examples, combinations of sensors 105 may be used to measure the response of the muscle to electrical stimulation and the controller 101 may identify motor points 106 and make other determinations based on the plurality of different types of measurements taken.

In one or more embodiments, the NMES system 102 may comprise one or more flex sensors. A flex sensor is a variable resistor wherein the resistance of the flex sensor varies based on the degree of flexing, or bending, that the sensor undergoes. The flex sensor may be incorporated into a number of different designs of a measurement circuit. In a simple type of measurement circuit, the flex sensor takes the place of a resistor in a potential divider arrangement wherein a first and second resistor are arranged in series between a supply voltage and a reference voltage, such as ground. An output voltage can be measured in parallel with the second resistor between the input to that resistor and ground. Where the flex sensor takes the place of the first resistor, such an output voltage is indicative of the amount of bending in the flex sensor. Because the muscle contracts upon receiving electrical stimulation, the flex sensor, which is incorporated into the garment in this embodiment, will bend, thereby providing an output measurement which can be provided to the controller 101 as a measurement signal. An electrical stimulation applied at two motor points 106 will provide for a greater stimulation, and therefore contraction, of the muscle compared to stimulation at non-motor point locations. As such, in an embodiment using at least one flex sensor, the controller 101 can identify the stimulation electrodes as those electrodes which provided for a flex of the flex sensor above a predetermined flex reaction threshold upon electrical stimulation. A plurality of flex sensors may be used in order to provide for increased reliability of the measurements. Where a plurality of pairs of electrodes provide for a flex above the flex reaction threshold, the first and second stimulation electrodes may further be selected as the pair of electrodes which provide for a flex above the flex reaction threshold that has the lowest voltage difference between the first and second electrodes. In this way, the minimum possible voltage can be selected which still corresponds to an acceptable stimulation. In other embodiments, the first and second stimulation electrodes may be selected as the first electrodes identified that meet the criteria of: providing for a flex above the flex reaction threshold; and having a voltage difference below an acceptable voltage threshold level. In this way, it may be possible to stop the motor point scan mode early if a pair of electrodes are identified which match both of the desired criteria of a sufficient flex and a sufficiently low voltage application.

In one or more embodiments, the NMES system 102 may comprise one or more electrical parameter sensors. By way of example, an electrical parameter sensor may comprise a resistivity sensor, a resistance sensor, a conductivity sensor, a conductance sensor or an impedance sensor. It will be appreciated that any other sensor that measures an electrical parameter indicative of the response of a muscle to electrical stimulation may equivalently be used. Because the electrical stimulation of a muscle by voltages applied at first and second electrodes in contact with the skin requires the lowest stimulation at the motor points to produce a given amount of muscle contraction, this gives the possibility that, in some instances, there may be a correlation between high conductivity between the electrodes and the motor points of a muscle. Correspondingly, then it will be appreciated that a high conductivity may be equivalent to a high conductance, a low resistivity or a low resistance. One or more of the electrodes of the electrode array 104 may be configured to operate as an electrical parameter sensor. For example, when a voltage is not applied to one of the electrodes, said electrode may be configured to take a measure of the conductivity of the muscle between the pair of electrodes which either at that time or recently had voltages applied therebetween. In some embodiments, it may only be possible for the electrode to operate as an electrical parameter sensor when no voltage is actively applied to the electrode for the provision of a current flow between the electrode and another electrode. In other examples, the one or more electrical parameter sensors may be distinct from the electrodes of the electrode array 104. For example, a sensor array may be provided comprising a plurality of electrical parameter sensors wherein each electrical parameter sensor is aligned with one or more of the electrodes of the electrode array 104 to take electrical parameter measurements.

In one or more embodiments, the NMES system 102 may comprise one or more fiber optic light sensors each comprising an optical fiber. The fiber optic light sensor may be arranged such that the optical fiber of the fiber optic light sensor will alter light transmission properties of the fiber optic light sensor upon contraction of the muscle. The controller may be configured to receive measurement signalling indicative of a degree of contraction of the fiber optic light sensor wherein, for example, a large contraction may result in a large change in the optical properties of the fibre optic light sensor and, as such, a significant change in the light transmitted by the optical fiber. The controller may be configured to identify the first and second stimulation electrodes based on the pair of first and second electrodes which provided change in the optical transmission of light via the optical fiber above or below a predetermined optical transmission threshold as measured by the fiber optic light sensor. It will be appreciated that movement of the optical fiber from a rest position could either increase or decrease the amount of light transmitted by the optical fibre and, as such, depending on the starting arrangement of the fibre, one might expect an amount of transmitted light to either be greater than or below a predetermined threshold. In one or more embodiments, the controller may be configured to identify the first and second stimulation electrodes based on the pair of first and second electrodes which provide a magnitude of a change of the optical transmission to be greater than a predetermined optical transmission threshold.

In one or more embodiments, the NMES system 102 may comprise a microphone sensor. The microphone sensor may be arranged such that it will detect one or more of a sound or vibrations upon contraction of the muscle. The controller may be configured to receive measurement signalling indicative of a motion in the muscle from the microphone sensor based on the one or more sounds or vibrations. The controller may be configured to identify the first and second stimulation electrodes based on the pair of first and second electrodes which provided for one or more of a sound and a vibration level above one or more of a respective sound threshold and a vibration threshold as measured by the microphone sensor.

In one or more embodiments, the NMES system 102 may comprise a microphone sensor, such as a blood-flow microphone sensor. The microphone sensor may be arranged such that it will detect one or more of changes in sound and vibrations originating from changes in blood flow in blood vessels associated with the muscle upon one or more of stimulation and contraction of the muscle. It will be appreciated that blood vessels associated with the muscle may be blood vessels which are directly adjacent to the muscle and the electrodes which are providing stimulation thereto. Alternatively, the blood vessels associated with the muscle may be blood vessels which are located away from the muscle and the electrodes but may be blood vessels that will receive an increase in blood flow as a result of stimulation by the NMES system. The controller may be configured to receive measurement signalling indicative of changes in blood flow from the at least one microphone sensor and wherein the controller is configured to identify the first and second stimulation electrodes based on the pair of first and second electrodes which provided for a blood flow above a blood flow threshold as measured by the microphone sensor.

Sensors 105 other than the flex sensor and electrical parameter sensors described may be used to measure the response of a muscle to electrical stimulation. For example, any sensor 105 which can measure the movement of a muscle may be suitable such as a photoresistor, which may detect changes in light indicative of the muscle moving towards or away from the photoresistor. Alternatively, one or more of the sensors 105 may be a sensor for electromyography, EMG, for example. In other embodiments, the one or more sensors 105 may be configured to measure peripheral blood circulation. Because the blood circulation is caused by the stimulation of the muscle, the blood flow may provide a helpful measure of the muscle stimulation. In one or more embodiments, one or more of the sensors 105 may be a blood sugar sensor such as a non-invasive blood sugar sensor. It has been identified that the muscles of the body act as organs that are involved in the metabolization of blood sugars and that the stimulation of the muscles increases metabolism of the blood sugars. As such, a blood sugar sensor may be capable of detecting changes in the blood sugar levels of the user and use this as an indicator of muscle stimulation.

One or more of the sensors 105 may be a piezoelectric sensor that may be configured to measure changes in one or more of pressure, acceleration, temperature, strain or force, each of which may be arranged on the muscle to measure these parameters, each of which could be indicative of stimulation of the muscle. Further, one or more of the sensors 105 may be another type of pressure sensor, such as a force sensing resistor, which may be arranged in a voltage divider arrangement to provide signalling to the controller 101 indicative of pressure applied to the sensor which may be applied or removed as a result of movement of the muscle.

The NMES system 102 may be configured to cause the electrode array 104 to operate in a motor point scan mode. The purpose of the motor point scan mode is to identify a first stimulation electrode and a second stimulation electrode wherein each stimulation electrode is aligned with a different motor point 106 of the muscle of the user. The alignment of an electrode with a motor point refers to that electrode being in suitable electrical contact with the motor point 106, such as being physically placed in contact with the skin over the motor point 106 or spatially proximal to the motor point 106 compared to other electrodes. An electrode that is aligned with a motor point 106 may be the electrode of the plurality of electrodes that is most closely aligned with the motor point as compared to any of the other electrodes of the electrode array 104. In some cases, a plurality of electrodes may be equally aligned, i.e. equidistant, with the motor point. In these examples, the controller 101 may be configured to select one of the plurality of equally aligned electrodes to be one of the first and second stimulation electrodes. In other embodiments, the controller 101 may be configured to designate a group-electrode as the first electrode wherein a group electrode is defined as a plurality of neighbouring or non-neighbouring electrodes of the electrode array 104 that, via signalling provided by the controller 101 to the NMES system 102, can be made electrically contiguous such that the application of a first voltage to a group-electrode comprises applying the first voltage to each of the electrodes of the group-electrode. For example, if two neighbouring or non-neighbouring electrodes are determined to be equidistant from a motor point by the identification that both provide a substantially identical reaction of the muscle to electrical stimulation, the controller 101 may make a selection between those two electrodes or it may designate that the two electrodes together are to be defined as a group-electrode for the designation of a first or second electrode for the stimulation mode. As discussed previously, each electrode in the electrode array 104 may be electrically isolated from its neighbouring electrodes and, as such, does not physically overlap with those neighbouring electrodes. As described above, in some examples the electrodes can be made electrically contiguous by the application of equal or near-equal voltages to contiguous neighbouring electrodes as a result of signalling provided by the controller 101 to the NMES system 102.

More specifically, a group-electrode made up of neighbouring (adjacently contiguous) electrodes would be particularly advantageous for a coarse motor point search where coverage of larger areas is desired. A group-electrode made up of non-neighbouring (non-adjacently contiguous) electrodes would be particularly advantageous when stimulating on several separate motor points simultaneously. Such examples will be described further below.

The motor point scan mode comprises performing a plurality of scan measurements wherein each scan measurement is taken using a different pair of electrodes from the plurality of electrodes. It will be appreciated that a pair of electrodes refers to the combination of a first electrode and a second electrode such that none of the measurement scans of the plurality of measurement scans trigger the same two electrodes in combination. For example, if electrode A is triggered contemporaneously with electrode B in a first scan measurement, then a subsequent scan measurement in the plurality of scan measurements will not use electrodes A and B again, however, they may use electrodes A and C or B and C. This description does not entirely limit repeat measurements being performed, however, there will be a plurality of measurements performed on different pairs of electrodes in order to provide for a scan of the possible electrode pairs.

In one or more embodiments the electrode array 104 may be caused to operate in a motor point scan mode such that all combinations of pairs of electrodes in the electrode array 104 are tested. Alternatively, the electrode array 104 may be divided into a first sub array and a second sub array, each sub array corresponding to a different portion of a muscle that the electrodes of the electrode array are expected to contact. In these embodiments, each electrode of the first sub-array may be tested with each electrode of the second sub-array such that each electrode pair comprises one electrode from each sub-array. This may provide for the avoidance of testing electrode pairs which would be expected to be associated with the same motor point 106, thereby providing for a more efficient scanning method.

During the motor point scan mode, a first measurement voltage is provided to one of the pair of electrodes, a first electrode, and a second measurement voltage is applied to the other electrode of the pair, a second electrode. As discussed, the first and second measurement voltages are different to provide an electrical potential difference that causes the electrical stimulation to the muscle or its innervation via the skin between the electrode pair.

The one or more sensors 105 may provide for measurement signalling to the controller 101 indicative of the response to the electrical stimulation for said pair of electrodes. Provision of the measurement signalling may be performed simply by providing a voltage to the controller 101 indicative of a measured value if the one or more sensors are in electrical contact with the controller 101. In other embodiments, the measurement signalling may comprise a wireless signal, for example, transmitted by a NMES controller to the controller 101.

The provision of measurement signalling to the controller 101 for each scan measurement will provide for a plurality of sets of measurement signalling at the controller 101. Based on the measurement signalling of each scan measurement, the controller 101 is configured to identify a first simulation electrode and a second stimulation electrode wherein each of the first stimulation electrode and second stimulation electrode is aligned with a different motor point of the muscle of the user, as previously discussed. The controller 101 is configured to identify the first and second stimulation electrodes based on the pair of electrodes which provide for a response above a flex reaction threshold by the muscles to the electrical stimulation.

The electrode array 104 is further configured to selectively operate in the stimulation mode based on signalling received by the NMES system 102 from the controller 101. In the NMES system 102, electrical stimulation is provided a plurality of times in succession to the user in order to provide for muscle contraction and increased blood flow. Each electrical stimulation may be referred to as the application of a stimulation signal wherein each stimulation signal comprises the application of a first stimulation voltage to the first stimulation electrode and a second stimulation voltage to the second stimulation electrode to provide the electrical stimulation to the muscle or its innervation via the skin between the first and second stimulation electrodes. The first stimulation voltage is different to the second stimulation voltage. It will be appreciated that the number of stimulations applied to the muscle will vary depending on the user and on the desired effect.

By providing for a controller 101 configured to provide signalling to control an NMES system 102 having an electrode array 104 and one or more sensors 105 as described herein, it is possible to provide a system which can identify the motor points before each stimulation mode quickly and efficiently. This allows for the NMES system 102 to be incorporated into a normal garment 103 which may move around during normal use without sacrificing accuracy of motor point stimulation. This not only provides for enhanced power saving due to the low power requirements of muscle stimulation at the motor points 106 but enhances comfort for a user, thereby increasing the chances of compliance.

The controller 101 may be configured to provide signalling to the NMES system 102 such that, for each stimulation signal after the first stimulation signal, the first stimulation voltage and the second stimulation voltage is swapped as compared to a preceding stimulation signal. The magnitudes of the first and second stimulation voltages may be the same as each other or they may be different. In some embodiments, the controller 101 may be configured to provide signalling to the NMES system 102 such that the first stimulation voltage and the second stimulation voltage are applied as square waves of opposing polarities. This may provide for particularly stable and consistent electrical stimulation. Alternatively, the stimulation voltages may be provided as sinusoidal AC voltages wherein each new application of a stimulation signal corresponds to the sinusoid passing through 0 volts. In yet other embodiments, the stimulation voltages may be applied in a DC manner.

The controller 101 may be configured to provide for the application of the stimulation signals at a fixed rate. For example, a rate of stimulation signal application may be between 1-100 Hz. In particular the rate of stimulation signal application may be 30-40 Hz and, more particularly, the rate of stimulation signal application may be 36 Hz. The application of the scan measurement during operation in a motor point scan mode may further be performed at the same rate as the applications of the stimulation signals, such as between 1-100 Hz, 30-40 Hz or 36 Hz.

The controller 101 may further be configured to provide for the control of one or more other parameters related to the application of stimulation signals or the signals used for each scan measurement. For example, the controller 101 may provide control of the phase-duration and inter-phase duration. The controller 101 may provide for control of the ramp-up time and the ramp-down time where these times correspond to the amount of time taken to get to the desired first and second voltages and down from the first and second voltages, respectively. The controller may also provide for control of the plateau time.

The voltages applied during each of the motor point scan mode and the stimulation mode may be predetermined voltage levels using standard levels expected to be suitable for an average user. In order to reduce discomfort to a user, the voltages applied to the electrodes during the motor point scan mode may be lower than those used during the stimulation mode. In this way, the user may experience the motor point scan mode as a series of very light stimulations that provide for very little musculature contraction while during the stimulation mode the muscle is made to contract to a degree which is medically effective. Alternatively, the user, or a person assisting the user in operation of the system 100, may be able to provide for control of one or both of the first and second stimulation voltages in order to control the electrical potential difference generated between the electrodes. The user or assistant may provide for this via a user interface device which may be configured to provide signalling to the controller 101 indicative of the desired stimulation voltages. The user interface device may be built into the garment 103 or it may form part of a separate device which may be the same device as that which the controller 101 is part of or a separate device. For example, a user may provide input indicative of their desired voltage via a mobile telephone or a tablet computer.

Alternatively, the controller 101 may be configured to obtain a calibration signalling which provides a baseline for the voltage which needs to be provided in order to achieve muscular stimulation. To this end, the controller 101 may be configured to provide signalling to cause the NMES system 102 to operate in a baseline stimulation mode. In the baseline stimulation mode, the controller 101 may be configured to receive measurement signalling from the NMES system 102 when no voltages are applied to the electrodes in response to signalling from the controller 101. In other words, the controller 101 may collect measurement signalling from the one or more sensors 105 when the NMES system 102 is at rest. This may provide for a baseline measurement from the sensors 105. In some examples, it may be particularly advantageous for the controller 101 to operate in the baseline stimulation mode when a user intentionally tenses the muscle to which the electrodes are connected via the skin. In such examples, the measurement signalling from the one or more sensors 105 may provide information indicative of the expected sensor values for a tensed or otherwise stimulated muscle. The controller 101 may be configured to provide signalling to an output device in order to instruct the user when to initiate the tensing. For example, the controller 101 may cause a speaker to provide a tone or other audio signal to indicate to the user that they should tense the muscle in question. In other examples, a visual display, haptic feedback or other sensory output may inform the user to tense the muscle in question. The controller 101 may also record measurements based on the one or more sensor outputs when the muscle is both tensed and not tensed in order to obtain a range of measurements. In other examples, the user may not be able to provide for user-induced stimulation during the calibration mode. For example, the user may be paralysed and so may not be able to take voluntary action. Based on the measurement signalling obtained during the baseline stimulation mode, the controller 101 may be configured to store the received measurement signalling as calibration signalling. It will be appreciated that this information may be stored on any suitable digital storage medium and that the controller 101 may process the measurement signalling prior to storing the calibration signalling.

During the operation in the stimulation mode, the controller 101 may be configured to compare the measurement signalling to the recorded calibration signalling. This may provide an alternative or additional way for the controller 101 to determine if a muscle has been sufficiently stimulated so as to provide the desired effect. If the measurement signalling obtained during the application of a stimulation signal is not within a predetermined threshold of the calibration signalling, the controller 101 may be configured to increase the magnitude of the voltage applied to the first and second electrodes during the application of a subsequent stimulation signal. The threshold may provide a tolerance of 10, 20 or 30% of the recorded calibration signalling or any other percentage. Alternatively, the threshold may be 0 percent, thereby requiring that any measurement signalling indicative of the stimulation of the muscle is at least equal to the recorded calibration signalling. It will be appreciated that the value in question may need to be higher or lower than the recorded calibration signalling, depending on the parameter being measured. For example, a conductivity may need to be within a predetermined threshold below the recorded calibration signalling or higher whereas a resistivity measurement may need to be within a predetermined threshold above the recorded calibration signalling or lower to be appropriate (because high conductivity may be correlated with a motor point 106 and low resistivity may similarly be correlated with a motor point 106). A low resistivity or corresponding high conductivity may be indicative of the presence of a motor point but it may not provide for a definitive measure of the optimum points for stimulation. In one or more embodiments, conductivity or resistivity measurements may be most beneficially employed by the controller as a secondary indicia of the optimum pairs of electrodes for electrical stimulation to be used alongside one or more other types of sensors.

In examples where the user did not provide for user-induced stimulation during the baseline stimulation mode, the controller 101 may be configured to require that stimulation induced by the NMES device 102 causes muscle contraction at least a predetermined amount above the calibration signalling. In this way, because the user was not able to provide for the user-induced stimulation, the controller 101 can look for a known amount of stimulation beyond the value of the calibration signalling which may relate to an average change expected when successful stimulation is induced by the system 100 on a user. For example, in the case of a flex sensor, this predetermined threshold may be related to an average amount of movement of the muscle which may be an expected amount of movement for an average user.

The controller 101 may be configured to apply the same voltage to the first and second electrodes during the application of subsequent stimulation signals as a voltage which causes the measuring signal to be within the predetermined threshold of the calibration signalling. That is, if a desired level of electrical stimulation is achieved, the controller 101 may be configured to maintain the stimulation voltage for future stimulation voltages, as higher voltages may be undesirable. There may be a threshold tolerance on either side of the calibration signalling indicative that a voltage may be too low to achieve electrical stimulation of the muscle or too high so as to potentially be dangerous to a user.

FIG. 4 shows an example electrode array 104 defining a 4×4 group-electrode 501, a 2×2 group electrode 502 and a motor point 106. The electrode array 104 may be configured such that a plurality of individual electrodes can have voltages applied thereto contemporaneously to define a larger group-electrode 501, 502. The voltages applied to the group electrode 501, 502 may be substantially identical. The electrical contiguity of the electrodes allows for the simulation of a single large electrode and may define the electrodes in any shape suitable for the stimulation of a motor-point. In one or more examples, the group-electrodes may be substantially spot-like as opposed to defining a line of electrodes. For example, the group-electrodes 501, 502 may be defined by a substantially square or circular grid, such as the 4×4 grid of electrodes 501 in a regular matrix electrode array 104. As described in more detail below, one or more group-electrodes 501, 502 may be used for improving the efficiency of identifying motor points 106 or may be used to provide for stimulation of larger areas on the body during a stimulation mode. In the case of certain muscle groups, it may provide for improved muscle stimulation to provide for stimulation of a single motor point 106 using a plurality of individual electrodes.

The controller 101 may be configured to provide signalling to the NMES system 102 to cause the electrode array 104 to operate in a group-electrode motor point scan mode. The group-electrode motor point scan mode operates in substantially the same way as the motor point scan mode except that, instead of selecting only a pair of electrodes to provide voltages to during each scan measurement, a pair of group-electrodes are defined instead. As such, the group-electrode motor point scan mode comprises providing a first measurement voltage to one group-electrode of a pair of group electrodes and providing a second measurement voltage to the other group-electrode of the pair. The first measurement voltage is different compared to the second measurement voltage to provide the electrical stimulation to the muscle or its innervation via the skin between the group-electrode pair. The scan measurement then comprises, based on a measurement performed by the one or more sensors 105, providing measurement signalling to the controller 101 indicative of the response to the electrical stimulation.

Based on the measurement signalling of each scan measurement of the group-electrode motor point scan mode received by the controller 101 from the NMES system 102, the controller 101 may be configured to identify a plurality of secondary group-electrodes wherein each secondary group-electrode is comprised of fewer electrodes than each group-electrode of the previous group-electrode motor point scan. Each of the secondary group-electrodes may be aligned with a motor point 106 of the muscle of the user, or at least signalling from the one or more sensors 105 indicative that a motor point 106 is aligned with those secondary group-electrodes. Because the number of individual electrodes making up the secondary group-electrodes is smaller than the number of electrodes making up the group-electrodes used in the group-electrode motor point scan mode (the group-electrodes may be referred to as primary group-electrodes in order to differentiate over the secondary group electrodes), the secondary group-electrodes may be wholly or partially contained within the group-electrodes that align with a motor point 106. FIG. 4 considers only a single group-electrode, rather than pairs of group electrodes, for simplicity of depiction. As demonstrated in FIG. 4, an 8×8 electrode array 104 would take 64 measurement scans to test every individual electrode in the array with a single electrode (and significantly more pair-combinations). In contrast, only four scan measurements are required if using a 4×4 group-electrode 501—one over each quadrant of the 8×8 grid. Based on the four scan measurements, the controller 101 may be configured to identify that the motor point 106 is in, for example, the fourth quadrant, as shown in the figure. At this point, a plurality of secondary group-electrodes 502 may be defined which are 2×2 group-electrodes 502 which are contained fully within the area defined by the group electrode 501 found to contain the motor point 106. Again, the quadrant containing the motor-point 106 can be entirely scanned by taking four group-electrode motor point scan measurements using the secondary electrodes 502 in order to identify a secondary electrode comprising the motor point therewithin. In the case of FIG. 4, the motor point 106 may be identified as being located in the first quadrant of the identified group electrode.

Considering pairs of electrodes again, in general terms, the controller 101 may be configured to identify two or more of the group-electrodes 501 which correspond to at least a first and a second motor point 106 and, based on the determination of the group-electrodes 501 associated with the motor points 106, determine smaller secondary group electrodes 502 which comprise electrodes contained within the identified two or more group-electrodes 501. By using this process, a more efficient scan mode may be achieved wherein large areas are scanned for broad correspondence to motor points and then smaller groups can be scanned to quickly find the best electrodes or group-electrodes for stimulation. It will be appreciated that this process could be repeated a plurality of times to reach steadily higher and higher resolution of scan. This may be more efficient than trying every possible pairing of electrodes together. It will be appreciated that the term secondary group-electrodes 502 is used herein to assist in differentiating the group-electrodes 501 used in a first group-electrode motor point scan mode from the smaller group-electrodes which may be identified based on that first group-electrode motor point scan mode. Further, one or more further group-electrode motor point scan modes may be performed after the group-electrode motor point scan mode using the secondary group-electrodes 502 which may define tertiary group-electrodes and so on. It will be appreciated that several different types of algorithms may be suitable for steadily increasing the resolution of a scan. This may be particularly beneficial for large electrode arrays 104 where a plurality of stages of group-electrode motor point scan modes may be particularly efficient.

Based on the plurality of sets of measurement signalling received by the controller 101 during a group-electrode motor point scan, the controller 101 may be configured to identify a sub-set of electrodes wherein each electrode of the sub-set of electrodes is associated with a motor point of the muscle of the user. This may be done after a group-electrode motor point scan mode using the group-electrodes 501, secondary-group electrodes 502 or later-stage group-electrodes. The controller 101 may be configured to provide signalling to the NMES system 102 to operate the electrode array 104 in a motor point scan mode using only the sub-set of electrodes. Referring to FIG. 4, this process refers to, for example, identifying a 2×2 matrix containing the motor point 106 and finally performing a motor point scan mode using only the single electrodes, as opposed to group-electrodes, of the 2×2 matrix. Thus, this step refers to a motor point scan mode at the highest resolution available to the electrode array 104 performed on the sub-set of electrodes identified during a previous group-electrode motor point scan. A normal stimulation mode may be performed after identifying the first and second stimulation electrodes aligned with different motor points.

Instead of providing for stimulation of motor points 106 using single electrodes during the stimulation mode, some muscles may be stimulated better by providing for stimulation over an area greater than that of a single electrode. As such, based on measurement signalling of each group-electrode scan measurement, the controller 101 may be configured to identify a first stimulation group-electrode and a second stimulation group-electrode where each group-electrode is aligned with a different motor point 106 of the muscle of the user. The controller 101 may then be configured to provide signalling to cause the NMES system 102 to operate the electrode array 104 in a group-electrode stimulation mode wherein the signalling causes a plurality of stimulation signals to be applied to the identified first and second stimulation group-electrodes. Each stimulation signal may comprise an application of a first stimulation voltage to the first stimulation group-electrode and a second stimulation voltage to the second stimulation group-electrode to provide electrical stimulation to the muscle or its innervation via the skin between the electrode pair and wherein the first stimulation voltage has a different polarity to the second stimulation voltage. It will be appreciated that the group-electrode stimulation mode is directly analogous to the stimulation mode previously described and, as such, modes related to the stimulation mode may equally be applied to the group-electrode stimulation mode, such as the baseline stimulation mode.

In one or more embodiments, during the motor point scan mode, the controller 101 may be configured to identify additional pairs of stimulation electrodes such as a second pair comprising third and fourth stimulation electrodes and optionally a third pair comprising fifth and sixth stimulation electrodes. The identification of the additional pairs of stimulation electrodes may be based on the same selection criteria as the first pair of electrodes. During the stimulation mode, the controller 101 may be configured to provide signalling to cause the stimulation signal to be applied to different pairs of stimulation electrodes in a successive manner such that a first pair of stimulation electrodes, comprising the first and second stimulation electrodes, has the first and second stimulation voltages applied thereto and subsequently, a second pair of stimulation electrodes may have the first and second stimulation voltages applied thereto. In other embodiments, the third and fourth electrodes making up the second pair of electrodes may have third and fourth voltages applied thereto, different to the first and second voltages. This may be advantageous because different points may require different voltage levels to induce a desired amount of muscle contraction. By stimulating different pairs of stimulation electrodes, higher strength gains may be obtained because the muscle is being worked more evenly over time. The stimulation of multiple pairs of electrodes may also decrease fatigue of particular parts of the muscle and improve contraction as a whole. This may also provide for improved blood flow.

In yet further embodiments, stimulation signals may be provided to multiple pairs of electrodes simultaneously or substantially consecutively, that is, one-after-another with a very short time period in between each other. The NMES system 102 may be configured to provide for simultaneous application of stimulation signals to pairs of stimulation electrodes in response to signalling received from the controller 101. In other embodiments, for example, the NMES system 102 may only be able to provide stimulation signals to a single pair of stimulation electrodes at a time but it may be configured to switch between pairs of electrodes as quickly as possible such that it is close to simultaneous stimulation. For example, the delay time between stimulation signals applied to different pairs of stimulation electrodes may be less than 1 ms. For example, the delay time between stimulation signals may be between 0.001 ms (1 μs) and 1 ms. In other embodiments, the delay time may be less than 0.001 ms.

It may be desirable to apply NMES to multiple different muscle sets in the body of a user. Indeed, the inventors of the present application have identified that surprisingly increased blood flow can be achieved by the application of NMES to a first muscle followed by another nearby muscle. For example, the application of NMES to the calves of a user followed by the application of NMES to the thigh can significantly improve blood flow. As such, it may be desirable to provide an NMES system 102 which can provide for the stimulation of two or more muscle sets. In some embodiments, the front of a user's calf may be stimulated in order to cause dorsiflexion of the ankles followed by the back side of the same calf in order to cause plantarflexion of the ankle. This has been shown to improve venous blood return.

It will be appreciated that some articles of clothing may cover multiple areas of the body, such as tights, long johns or a body suit. As such, a single garment 103 may comprise two or more electrode arrays 104 and associated sensors 105 wherein each electrode array 104 is incorporated into the garment such that they are arranged to provide for electrical stimulation to different muscles. In other embodiments, the NMES system 102 may comprise a second garment (or more garments) wherein the second garment provides a support for the relative arrangements of the electrodes of a second electrode array and associated one or more sensors such that the second garment provides for the distribution of the electrodes over at least a body part of the user different to the body part which the electrodes of the first electrode array 104 are extended over. That is, the NMES system 102 may comprise, for example, a sock comprising a first electrode array 104 and associated one or more sensors 105 and a pair of boxer shorts comprising a second electrode array and a corresponding one or more sensors 105.

The first and second electrode arrays 104 may be configured to work independently of each other such that the second electrode array may receive signalling to cause it to operate in a motor point scan mode, a stimulation mode or a calibration mode, for example, without correlation to the modes being performed by the first electrode array 104.

In other embodiments, the first and second electrode arrays 104 may be configured to operate in a sequential stimulation mode wherein the signalling provided by the controller 101 causes a plurality of stimulation signal sequences to be applied to the first electrode array 104 and the second electrode array. Each stimulation signal sequence may comprise an application of a first stimulation voltage to a first stimulation electrode of the first electrode array and a second stimulation voltage to the second stimulation electrode of the first electrode array to provide electrical stimulation to the muscle or its innervation via the skin between the first stimulation electrode and the second stimulation electrode. The first stimulation voltage is different to the second stimulation voltage. This may correspond, for example, to the application of stimulation voltages to first and second electrodes of a sock garment 103 such that a calf muscle is caused to contract, thereby encouraging blood flow through the lower leg. The stimulation signal sequence may subsequently comprise applying a first stimulation voltage to the first stimulation electrode of the second electrode array and a second stimulation voltage to the second stimulation electrode of the second electrode array in order to provide electrical stimulation to the muscle or its innervation via the skin between the first stimulation electrode and the second stimulation electrode of the second electrode array. As previously provided for, the first stimulation voltage will be different to the second stimulation voltage. This use of the second electrode array may correspond to the application of stimulation voltages to the first and second electrodes of a pair of boxer shorts such that a thigh and/or a gluteal muscle is caused to contract, thereby encouraging blood flow through the upper leg.

The voltages applied to the first and second electrodes of the first electrode array 104 and those applied to the first and second electrodes of the second electrode array have been referred to as first and second voltages in line with the description of their identification in the motor point scan mode which can be equally performed on either the first or second electrode array 104. It will be appreciated that the voltages applied to the first electrode array 104 may be the same or different to the electrodes that are applied to the second electrode array. For example, the muscle associated with the second electrode array may require a higher voltage to provide for a desired level of stimulation to the muscle. The first and second voltages applied to the second electrode array may alternatively be referred to as third and fourth voltages to differentiate them in nomenclature from those applied to the first electrode array.

In some embodiments, the controller 101 may be configured to cause the NMES system 102 to operate in the motor point scan mode followed by the stimulation mode according to a predetermined schedule. For example, the controller 101 may cause a search for motor points 106 and subsequent muscle stimulation every 30 minutes, every hour, every two hours or at any other interval. This may be particularly helpful for patients who cannot voluntarily stimulate their muscles.

In order to prevent problems caused by inactivity, the controller 101 may be configured to detect inactivity of the user and, if the user has been inactive for a predetermined period of time, the controller 101 may be configured to initiate at least a stimulation mode. In particular, the controller 101 may be configured to cause the NMES system 102 to operate in a monitoring mode wherein, during the monitoring mode, the controller 101 is configured to not provide signalling to cause the NMES system 102 to apply voltages at any of the electrodes. During the monitoring mode, the controller 101 is further configured to receive signalling from the one or more sensors 105 one of continuously and periodically. It will be appreciated that either continuous or periodic monitoring of the activity of the user can both provide for valuable monitoring of the activity of the user. The NMES system 102 may operate in this monitoring mode by default when not operating in a calibration mode, motor point scan mode or stimulation mode. If the controller 101 receives no indication of user-induced stimulation within a predetermined monitoring time, the controller 101 may be configured to cause the NMES system 102 to operate in the stimulation mode. The predetermined monitoring time may be, for example, 30 minutes, one hour, two hours, three hours or any other suitable time based on the needs of the user.

In one or more embodiments, during the monitoring mode, the controller 101 may further be configured to receive one or more resistance measurements from the electrodes of the electrode array 104. The controller 101 may be configured to determine whether the electrodes of the electrode array 104 are in contact with the skin of a user based on the resistance measurements falling within an expected resistance range. For example, a resistance that is too low may be indicative of a short circuit and a resistance that is too high may be indicative that the electrodes are not connected to a user's skin and, instead are not connected to anything or are connected to an insulator. The expected resistance range may comprise resistance values that would be considered typical when coupled to a user's body. It will be appreciated that a measurement of conductance, conductivity, resistivity or impedance may equally be used to determine if the electrodes of the electrode array 104 is applied to a user's body.

In some examples, because the controller 101 has determined a period of non-activity by the user, the NMES system 102 may not need to operate in the motor point scan mode again if no user-initiated stimulation has occurred since a previous motor point scan mode was performed. For example, the lack of indication of user-initiated stimulation as detected by the one or more sensors 105 may be indicative that the user has not moved and, as such, it may be expected that the previously identified stimulation electrodes of stimulation group-electrodes may still be aligned with the motor points, i.e., the user's garment will not have been moved. Where this is the case, it may not be necessary to re-identify the first and second stimulation electrodes and so the controller 101 can move straight to the stimulation mode. In other examples, the controller 101 may be configured to operate in the motor point scan mode directly prior to each stimulation mode.

User-induced stimulation refers to a contraction of the muscle caused by the user purposefully using the muscle in question. A movement may only be considered to be a user-induced stimulation if the controller 101 determines, based on signalling from the or each sensor 105, that the contraction is within a predetermined threshold of the calibration signalling. The calibration signalling is signalling indicative of the contraction of the muscle by the user during a calibration mode. That is, small amounts of movement by a user (below a flex reaction threshold or a threshold of the calibration signalling) may not be sufficiently stimulating to provide for desired blood flow or exercise of the muscle. In such circumstances, it may be desirable to have the NMES system 102 operate in the stimulation mode. In some examples, registered contraction of the muscle that is below the predetermined threshold of the calibration signalling over a predetermined upper contraction duration may be registered as a user-induced stimulation, as this may be indicative of small-scale exercise over an extended period that is sufficient to obviate the need of additional stimulation by the electrode array 104. That is, movement by the user by small amounts (below a threshold) for an extended period of time may be deemed to be acceptable to cause the desired blood flow, exercise or other stimulation effect for the user such that stimulation by the NMES system 102 is deemed to be unnecessary.

In one or more embodiments, the controller 101 may be configured to access a motor point database stored in memory. The motor point database may comprise information indicative of an expected correlation of each electrode with a motor point. Each electrode of the electrode array 104 may be associated in the motor point database with a probability of there being a motor point at that position where, for example, the probability may be represented as a decimal number or as a percentage. The motor point database may be generated based on a previous motor point scan mode or it may be a pre-generated database based on average data taken from a plurality of users in the past. The controller 101 may be configured to determine the first and second stimulation electrodes at least partially based on data from the motor point database. For example, where two pairs of electrodes provide for similar degrees of stimulation according to the one or more sensors 105, the controller 101 may be configured to select the first and second stimulation electrodes based on the pair of electrodes which have the highest probability of being located at or near a motor point according to the motor point database. Additionally or alternatively, the controller 101 may be configured to select the order of pairs of electrodes to test during the motor point scan mode based on the pairs of electrodes that have the highest probability of being at a motor point according to the motor point database. This may improve the probability of identifying first and second stimulation electrodes quickly. For example, where the controller 101 is configured to select the first pair of electrodes that meet certain requirements (such as meeting a flex reaction threshold and being within an acceptable voltage range to induce stimulation) as the first and second stimulation electrodes, making use of the motor point database may allow the controller 101 to find an acceptable pair of electrodes quickly.

One or more components of the NMES system 102 may be formed in the garment 103 by the arrangement of conductive fibres. For example, the electrodes or sensors, such as the flex sensors, and interconnecting fibre wiring may be implemented as fibretronic devices.

Figure 5:
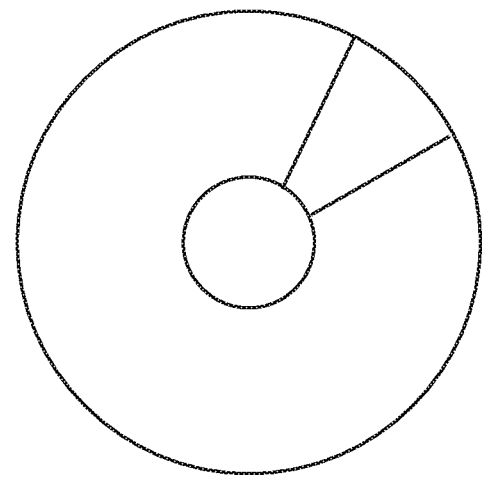
FIG. 5 shows an example embodiment of a computer readable medium.

FIG. 5 shows a computer readable medium comprising computer program code configured to cause a controller comprising a processor and a memory to operate as described herein.

Figure 6:
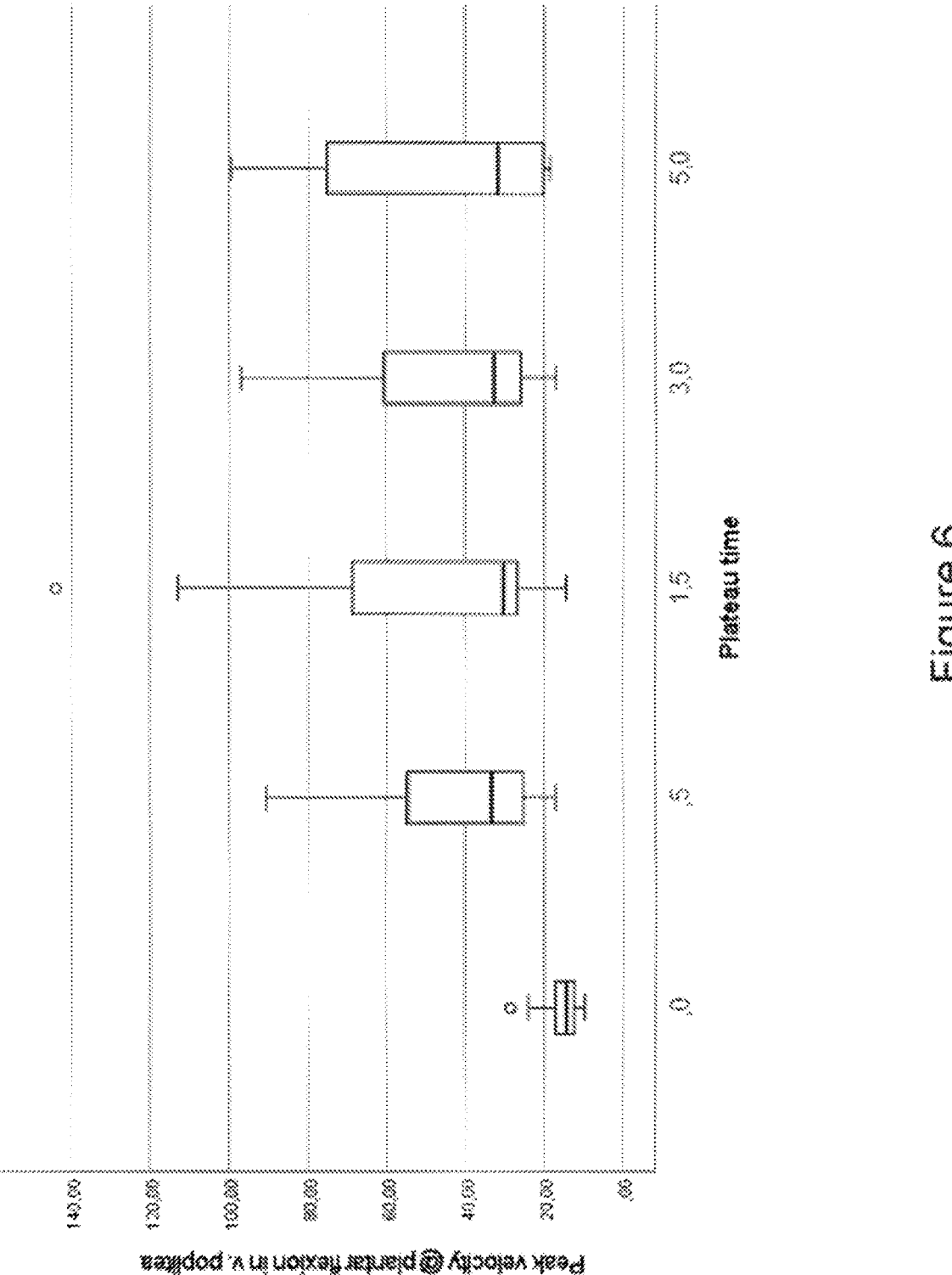
FIG. 6 shows data representative of the peak blood flow velocity in the popliteal vein induced by a NMES system of this disclosure against stimulation time.

FIG. 6 shows the increase in the median peak velocity of blood flow in the popliteal vein as compared to a baseline measurement. Peak blood flow velocity is provided along the y axis and plateau time is provided along the x axis. This figure shows that significantly increased blood flow is achieved by the application of NMES to one or more muscles in the vicinity of the popliteal vein.

The invention claimed is:

1. A controller for providing signalling to and receiving signalling from at least one electrical stimulation, ES, system, comprising an electrode array of a plurality of electrodes for applying an electrical stimulation to a muscle and one or more sensors for detecting a response of the muscle to said electrical stimulation;

wherein the controller is configured to provide signalling to the ES system to selectively operate the electrode array in one of a motor point scan mode or a stimulation mode, wherein the motor point scan mode comprises a mode, wherein the signalling causes a plurality of scan measurements to be taken between different pairs of the plurality of electrodes, wherein a pair of the plurality of electrodes is the combination of a first electrode and a second electrode selected from any electrodes of the electrode array wherein, when the controller selects a subsequent scan measurement, the corresponding electrode pair for that subsequent scan measurement comprises a pair of any two electrodes of the electrode array except for any pairing which would correspond to a previously taken scan measurement of the motor point scan, and wherein each scan measurement comprises:

providing a first measurement voltage to one electrode of the pair and providing a second measurement voltage to the other electrode of the pair, the first measurement voltage being different than the second measurement voltage so as to provide the electrical stimulation to the muscle between the electrode pair; and based on a measurement performed by the sensor or sensors, providing measurement signalling to the controller indicative of the response to the electrical stimulation for said pair of electrodes, based on the measurement signalling of each scan measurement received by the controller, the controller is configured to identify a first stimulation electrode and a second stimulation electrode, wherein each of the first stimulation electrode and second stimulation electrode is aligned with a different motor point of the muscle of the user; and the stimulation mode comprises a mode, wherein the signalling causes a plurality of stimulation signals to be applied, wherein each stimulation signal comprises:

an application of a first stimulation voltage to the first stimulation electrode and a second stimulation voltage to the second stimulation electrode to provide the electrical stimulation to the muscle between the first and second stimulation electrodes and, wherein the first simulation voltage is different than the second stimulation voltage.

2. The controller of claim 1, wherein the ES system further comprises a first garment, wherein the first garment provides a support for the relative arrangement of the electrodes and sensor or sensors and the first garment is configured to distribute at least the electrodes over at least a body part of the user.

3. The controller of claim 1, wherein during the stimulation mode, the controller is configured to provide signalling to the ES system such that, for each stimulation signal after a first stimulation signal, the polarity of the first stimulation voltage and the second stimulation voltage is swapped as compared to the preceding stimulation signal.

4. The controller of claim 3, wherein during the stimulation mode, the controller is configured to provide signalling to the ES system such that the first stimulation voltage and the second stimulation voltage are each applied as square waves.

5. The controller of claim 1, wherein the contemporaneous application of identical voltages to a plurality of electrodes in the electrode array define a group-electrode and, wherein the controller is configured to provide signalling to the ES system to operate the electrode array in a group-electrode motor point scan mode, wherein:

the group-electrode motor point scan mode comprises a mode, wherein the signalling causes a plurality of scan measurements to be taken between different pairs of group-electrodes of the electrode array and, wherein each scan measurement comprises:

providing a first measurement voltage to one group-electrode of the pair and providing a second measurement voltage to the other group-electrode of the pair, wherein the first measurement voltage is different than the second measurement voltage so as to provide the electrical stimulation to the muscle between the electrode pair; and based on a measurement performed by the sensor or sensors, providing measurement signalling to the controller indicative of the response to the electrical stimulation.

6. The controller of claim 5, wherein based on the measurement signalling of each scan measurement received by the controller from the ES system during a group-electrode motor point scan mode, the controller is configured to identify a plurality of secondary group-electrodes, wherein each secondary group-electrode is comprised of fewer electrodes than each group-electrode of the previous group-electrode motor point scan and each of the secondary group-electrodes is aligned with a motor point of the muscle of the user, and wherein the controller is configured to provide signalling to the ES system to operate the electrode array in the group-electrode motor point scan mode using the determined plurality of secondary group-electrodes.

7. The controller of claim 5, wherein based on the plurality of sets of measurement signalling received by the controller from the ES system during the group-electrode motor point scan mode, the controller is configured to identify a sub-set of electrodes, wherein each electrode of the sub-set of electrodes is associated with a motor point of the muscle of the user and, wherein the controller is further configured to provide signalling to the ES system to operate the electrode array in a motor point scan mode using only the sub-set of electrodes.

8. The controller of claim 5, wherein based on measurement signalling of each group-electrode scan measurement, the controller is configured to identify a first stimulation group-electrode and a second stimulation group-electrode, wherein each of the first stimulation group-electrode and second stimulation group-electrode is aligned with a different motor point of the muscle of the user and, wherein the controller is configured to provide signalling to cause the ES system to operate the electrode array in the group-electrode stimulation mode, wherein the group-electrode stimulation mode comprises a mode, wherein the signalling causes a plurality of stimulation signals to be applied to the identified group-electrodes and, wherein each stimulation signal comprises:

an application of a first stimulation voltage to the first stimulation group-electrode and a second stimulation voltage to the second stimulation group-electrode to provide electrical stimulation to the muscle between the electrode pair and, wherein the first stimulation voltage is different than the second stimulation voltage.

9. The controller of claim 1, wherein at least one sensor comprises:

a flex sensor, wherein the flex sensor is configured to flex upon contraction of the muscle and, wherein the controller is configured to receive measurement signalling indicative of the degree of flex of the flex sensor and, wherein the controller is configured to identify the first and second stimulation electrodes based on the pair of first and second electrodes, which provided for a flex above a flex reaction threshold, as measured by the flex sensor, a fiber optic light sensor comprising an optical fiber, wherein the fiber optic light sensor is arranged such that the optical fiber of the fiber optic light sensor will alter light transmission properties of the fiber optic light sensor upon contraction of the muscle and, wherein the controller is configured to receive measurement signalling indicative of a degree of contraction of the fiber optic light sensor and, wherein the controller is configured to identify the first and second stimulation electrodes based on the pair of first and second electrodes, which provide change in the optical transmission of light via the optical fiber above or below a predetermined optical transmission threshold, as measured by the fiber optic light sensor, a microphone sensor, wherein the microphone sensor is configured to detect sound or vibration or both upon contraction of the muscle and, wherein the controller is configured to receive measurement signalling indicative of a motion in the muscle from the microphone sensor and, wherein the controller is configured to identify the first and second stimulation electrodes based on the pair of first and second electrodes, which provided for a sound or a vibration level or both above a respective sound threshold or a vibration threshold or both, as measured by the microphone sensor, or a microphone sensor, wherein the microphone sensor is configured to detect a change in sound or vibration or both originating from a change in blood flow in one or more blood vessels associated with the muscle upon stimulation or contraction of the muscle or both and, wherein the controller is configured to receive measurement signalling indicative of a change in blood flow from the at least one microphone sensor and, wherein the controller is configured to identify the first and second stimulation electrodes based on the pair of first and second electrodes, which provided for a blood flow above a blood flow threshold, as measured by the microphone sensor.

10. The controller of claim 1, wherein at least one sensor is an electrical parameter sensor, wherein the electrical parameter sensor is one of:

a resistivity sensor configured to determine an electrical resistivity and, wherein the controller is configured to identify the first and second stimulation electrodes based on the pair of electrodes, which provide for a resistivity below an acceptable resistivity threshold;

a resistance sensor configured to determine an electrical resistance and, wherein the controller is configured to identify the first and second stimulation electrodes based on the pair of electrodes, which provide for a resistance below an acceptable resistance threshold;

a conductivity sensor configured to determine an electrical conductivity and, wherein the controller is configured to identify the first and second stimulation electrodes based on the pair of electrodes which provide for a conductivity above an acceptable conductivity threshold;

a conductance sensor configured to determine an electrical conductance and, wherein the controller is configured to identify the first and second stimulation electrodes based on the pair of electrodes, which provide for a conductance above an acceptable conductance threshold; and an impedance sensor configured to determine an electrical impedance and, wherein the controller is configured to identify the first and second stimulation electrodes based on the pair of electrodes, which provide for an impedance below an acceptable impedance threshold.

11. The controller of claim 10, wherein one of the electrodes of the electrode array is configured to operate as an electrical parameter sensor.

12. The controller of claim 11, wherein a plurality of the electrodes of the electrode array are configured to operate as electrical parameter sensors.

13. The controller of claim 1, wherein the controller is configured to provide signalling to cause the ES system to operate in a baseline stimulation mode wherein, in the baseline stimulation mode, the controller is configured to receive measurement signalling from the ES system when no voltages are applied to the electrodes in response to signalling from the controller and the controller is configured to record the received measurement signalling as calibration signalling wherein, during operation in the stimulation mode, the controller is configured to compare the measurement signalling to the recorded calibration signalling and if the measurement signalling is not within a predetermined threshold of the calibration signalling, the controller is configured to increase the magnitude of the voltage applied to the first and second electrodes during the application of a subsequent stimulation signal or if the measurement signalling is within a predetermined threshold of the calibration signalling, the controller is configured to apply the same voltage to the first and second electrodes during the application of subsequent stimulation signals as the voltage, which caused the measuring signalling to be within the predetermined threshold of the calibration signalling.

14. The controller of claim 1, wherein the electrode array is a first electrode array and ES system further comprises a second electrode array of a plurality of electrodes for applying electrical stimulation to the muscle and one or more second sensors for detecting a response of a muscle to said electrical stimulation, wherein the first electrode array and second electrode array in the ES system are configured to stimulate different muscles, wherein the controller is configured to provide signalling to cause the ES system to selectively operate the second electrode array in one of the motor point scan mode or the stimulation mode.

15. The controller of claim 14, wherein the controller is configured to cause the ES system to operate in a sequential stimulation mode, wherein the sequential stimulation mode comprises a mode, wherein the signalling causes a plurality of stimulation signal sequences to be applied to the first electrode array and the second electrode array, wherein each stimulation signal sequence comprises:

an application of the first stimulation voltage to the first stimulation electrode of the first electrode array and a second stimulation voltage to the second stimulation electrode of the first electrode array to provide the electrical stimulation to the muscle between the first stimulation electrode and the second stimulation electrode; and wherein the first simulation voltage is different than the second stimulation voltage followed by an application of a first stimulation voltage to the first stimulation electrode of the second electrode array and a second stimulation voltage to the second stimulation electrode of the second electrode array to provide electrical stimulation to the muscle between the first stimulation electrode and the second stimulation electrode of the second electrode array, wherein the first simulation voltage is different than the second stimulation voltage and, wherein the first voltage and the second voltage applied to the first and second electrodes of the second electrode array are one of:

the same magnitudes as the first voltage and second voltage applied to the first electrode and second electrode of the first electrode array or different magnitudes to the first voltage and second voltage applied to the first electrode and second electrode of the first electrode array.

16. The controller of claim 1, wherein the controller is configured to cause the ES system to operate in a monitoring mode, wherein during the monitoring mode, the controller is configured to provide signalling to cause the ES system to apply voltages at any of the electrodes and the controller is further configured to receive signalling from the sensor or sensors continuously or periodically and, wherein, if the controller receives no indication of user-induced stimulation within a predetermine monitoring time, the controller is configured to cause the ES system to operate in the stimulation mode.

17. An electrical stimulation, ES, system for receiving signalling from and providing signalling to a controller wherein the controller comprises the controller of claim 1 and the ES system comprises an electrode array of a plurality of electrodes configured to apply electrical stimulation to the muscle and one or more sensors for detecting a response of a muscle to said electrical stimulation.

18. The ES system of claim 17 further comprising a garment, wherein the garment provides a support for the electrodes and sensor or sensors and is configured to distribute at least the electrodes over at least a body part of the user.

19. A system comprising the electrical stimulation system of claim 17.

20. A computer readable medium comprising a computer program code configured to cause the controller of claim 1 to operate.

* * * * *